(12) United States Patent
Aron et al.

(10) Patent No.: US 7,221,982 B2
(45) Date of Patent: May 22, 2007

(54) APPARATUS AND METHOD OF COATING IMPLANTABLE LEADS

(75) Inventors: Rebecca Aron, Minneapolis, MN (US); Jeffrey P. Bodner, St Paul, MN (US); Mohan Krishnan, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/889,504

(22) Filed: Jul. 12, 2004

(65) Prior Publication Data

US 2006/0009829 A1 Jan. 12, 2006

(51) Int. Cl.
*A61N 1/00* (2006.01)

(52) U.S. Cl. ...................................... 607/116

(58) Field of Classification Search ................ 607/116, 607/117, 119; 600/373–377
See application file for complete search history.

(56) References Cited

U.S. PATENT DOCUMENTS

| | | | | |
|---|---|---|---|---|
| 4,643,202 A * | 2/1987 | Roche | ......................... | 607/116 |
| 5,358,516 A * | 10/1994 | Myers et al. | ............... | 607/116 |
| 6,049,736 A * | 4/2000 | Stewart et al. | ............... | 607/116 |
| 6,148,237 A * | 11/2000 | Das | ............................ | 607/122 |
| 6,506,457 B2 | 1/2003 | Hum | | |
| 6,549,811 B2 * | 4/2003 | Stewart et al. | ............... | 607/116 |
| 6,664,335 B2 | 12/2003 | Krishnan | | |
| 2003/0199959 A1 * | 10/2003 | Zhang et al. | ............... | 607/122 |

\* cited by examiner

*Primary Examiner*—Mark Bockelman
(74) *Attorney, Agent, or Firm*—Schwegman, Lundberg, Woessner & Kluth, P.A.

(57) ABSTRACT

An implantable cardiac lead, and/or subassembly includes an elongate sheath of insulative material including an insulative first layer and a protective second layer. The insulative first layer has at least one adhesive enhancing activated surface.

36 Claims, 3 Drawing Sheets

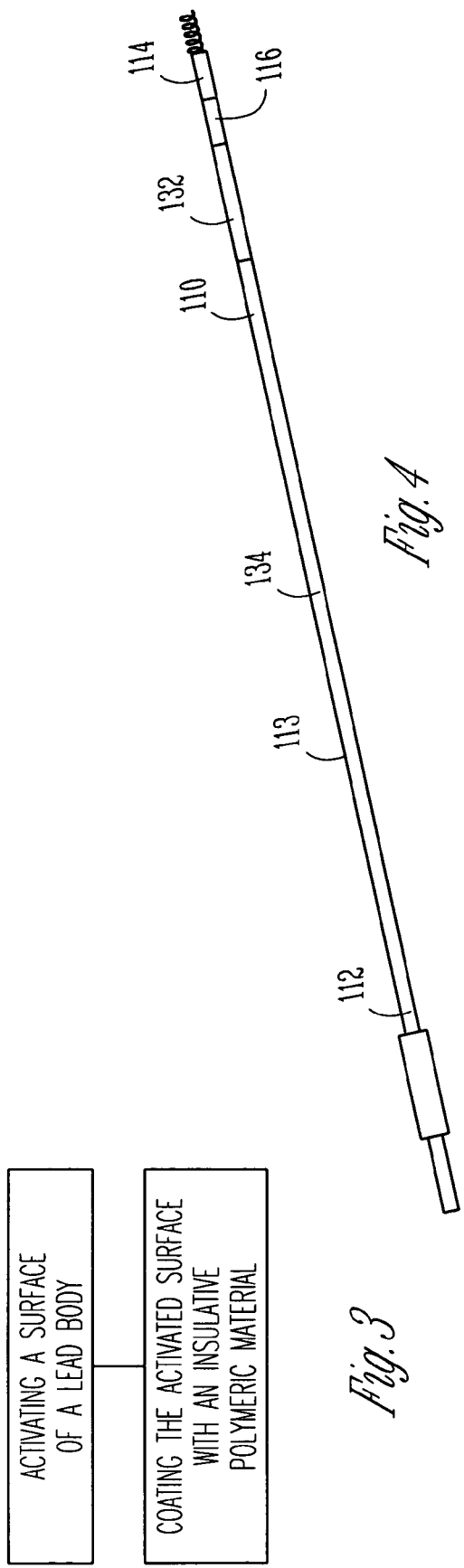
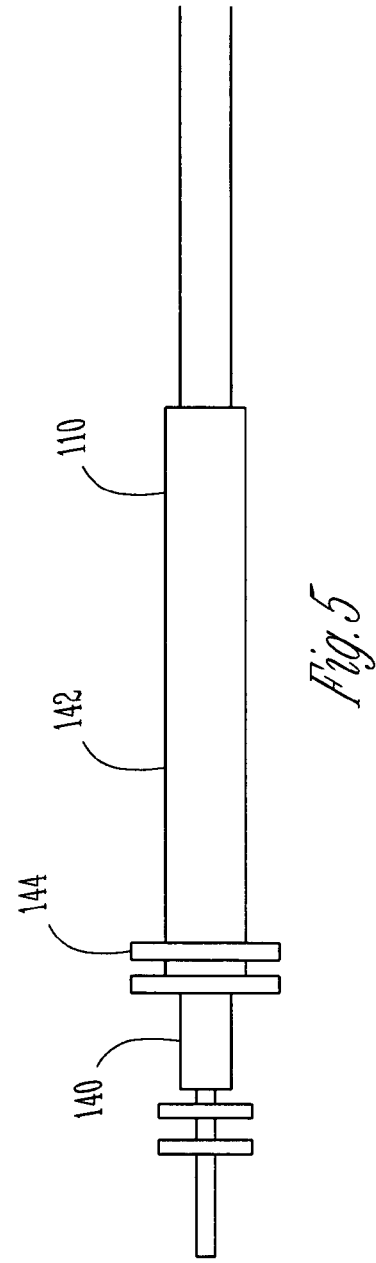
Fig. 3
ACTIVATING A SURFACE OF A LEAD BODY
COATING THE ACTIVATED SURFACE WITH AN INSULATIVE POLYMERIC MATERIAL
Fig. 4
Fig. 5

APPARATUS AND METHOD OF COATING IMPLANTABLE LEADS

TECHNICAL FIELD

The present subject matter relates to leads for stimulating or monitoring tissue. More particularly, it pertains to an apparatus and method of coating leads.

BACKGROUND

Leads implanted in or about the heart have been used to reverse certain life threatening arrhythmias, or to stimulate contraction of the heart. Electrical energy is applied to the heart via the leads to return the heart to normal rhythm. Leads have also been used to sense in the atrium or ventricle of the heart and to deliver pacing pulses to the atrium or ventricle.

The lead includes one or more conductors to conduct energy from the pacemaker to the heart, and also to receive signals from the heart. In a typical construction, one conductor goes to the band electrode proximally (outer electrode) and another conductor goes to the tip electrode at the distal end (inner electrode). The conductors run side by side and are insulated from each other and also from the body. The insulation is typically a polymer tubing or covering over the lead body. These polymeric materials must demonstrate resistance to hydrolysis and degradation by oxides found in the body. These polymeric materials must also demonstrate appropriate mechanical and electrical properties for use as electrical stimulation leads.

Silicone rubber and polyurethanes have been used most commonly to insulate leads. The silicone rubbers have excellent biocompatibility and long-term stability but they have weak tensile strength and low abrasion resistance. Polyurethanes are less thrombogenic than silicone rubber and higher in tensile strength. In addition, they slide easily against one another when moistened with body fluids. However, polyurethanes tend to be stiffer and not as pliable as silicone rubber.

Currently, leads are sometimes manufactured with a proximal polyurethane section and a distal silicone section. To achieve the required insulative properties, separate silicone and polyurethane composite tubing are layered over the lead.

Accordingly, there is a need for a lead insulation that has flexible material resistance and has improved lubricity.

SUMMARY

An implantable cardiac lead is provided that includes an elongate sheath of an insulated first layer of material, where the elongate sheath extends from a proximal end to a distal end and includes an intermediate portion therebetween. The elongate sheath is defined in part by an outer surface and an inner surface. An elongate conductor is located within the elongate sheath, and an electrical connector is coupled to the conductor. The insulating first layer includes an adhesive enhancing activated surface.

Several options for the implantable cardiac lead are as follows. For instance, in one option, the adhesive enhancing activated surface is manufactured via plasma assisted chemical vapor deposition treatment, for instance with the monomers including but not limited to acrylic acid, allyl amine, acrylamide, acrylonitrile, methacrylic acid, glycidyl methacrylate, N,N-dimethylacrylamide, and acetylene. In another option, the adhesive enhancing activated surface is manufacture via chemical treatment. In another option, the activated surface includes a recess portion, and a second layer of material is disposed within the recess portion. In yet another option, the lead further comprises a terminal area with a connector, and a second layer of material is applied to the terminal area of the lead.

In another option, an implantable cardiac lead subassembly is provided that includes an elongate flexible body extending from a proximal end to a distal end and defined in part by an outer surface and an inner surface. In one option, at least a portion of the outer surface or the inner surface has an activated surface that is covered by a second coating of material, such as polyurethane. Further options include providing first and second layers of material that transition from a combination of polyurethane and silicone to silicone only.

In another embodiment, a method is provided that includes providing a flexible lead body having a surface, an increasing adhesion of the surface including activating the surface of the flexible lead body. The method further includes coating a second layer of material, such as a protective material on the activated surface of the flexible lead body.

Several options are as follows. For instance, the method further includes activating the surface of the flexible lead body using plasma assisted chemical vapor deposition, or treating the surface of the flexible lead body with a monomer. In one option, the monomer includes at least one of acrylic acid, allyl amine, acrylamide, acrylonitrile, methacrylic acid, glycidyl methacrylate, N,N-dimethylacrylamide, and acetylene. Subsequent processing may include coating the surface with at least one of polyurethane and silicone. In yet another option the coating is disposed along only a portion of the lead body. In yet another option the coating is coated only on a distal area of a flexible lead body.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE FIGURES

FIG. 3 illustrates a flow diagram for a method in accordance with at least one embodiment.

FIG. 4 illustrates an elevational view of a lead constructed in accordance with at least one embodiment.

FIG. 5 illustrates a side-elevational view of a portion of a lead constructed in accordance with at least one embodiment.

DETAILED DESCRIPTION

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope is defined by the appended claims.

Figure 1:
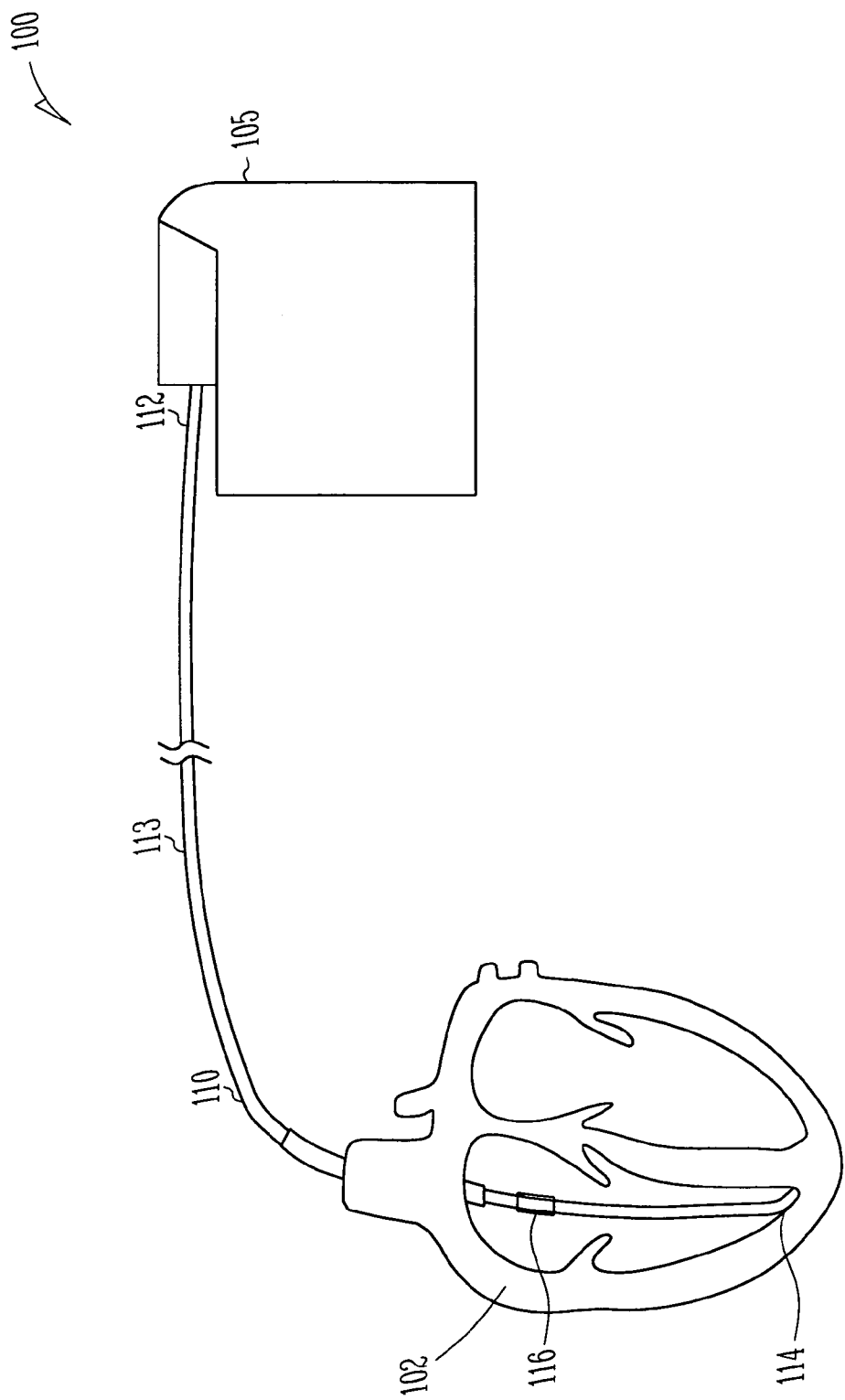
FIG. 1 illustrates a block diagram of a lead assembly constructed in accordance with an embodiment.

A lead assembly 110 and lead system 100 are illustrated in FIG. 1. FIG. 1 is a diagram of a system 100 for delivering and/or receiving electrical pulses or signals to stimulate, shock, and/or sense the heart 102. The system 100 includes a pulse generator 105 and a lead 110. The pulse generator 105 includes a source of power as well as an electronic circuitry portion. The pulse generator 105, in one option, is a battery-powered device which generates a series of timed electrical discharges or pulses. The pulse generator 105 is generally implanted into a subcutaneous pocket made in the wall of the chest. Alternatively, the pulse generator 105 is placed in a subcutaneous pocket made in the abdomen, or in other locations. It should be noted that while the lead assembly 110 is illustrated for use with a heart, the lead assembly 110 is suitable for other forms of stimulation as well. For example, the lead assembly 110 can be used for neuro stimulation.

The lead assembly 110 includes a lead body 113 which extends from a proximal end 112, where it is coupled with the pulse generator 105, as further discussed below. The lead assembly 110 extends to a distal end 114, which is coupled with a portion of a heart 102, when implanted or otherwise coupled therewith. Disposed along a portion of the lead body 113, for example near the distal end 114 of the lead assembly 110 includes at least one electrode assembly 116 which electrically couples the lead assembly 110 with the heart 102. At least one electrical conductor 118 (FIG. 2A) is disposed within the lead assembly 110 and extends, in one option, from the proximal end 112 to the distal end 114 of the lead assembly 110. The at least one electrical conductor 118 electrically couples the electrode assembly 116 with the proximal end 112 of the lead assembly 110. The electrical conductors carry electrical current and pulses between the pulse generator 105 and the electrode assembly 116, and to and from the heart 102. In one option, the at least one electrical conductor 118 is a coiled conductor. In another option, the at least one electrical conductor 118 includes one or more cables.

Figure 2A:
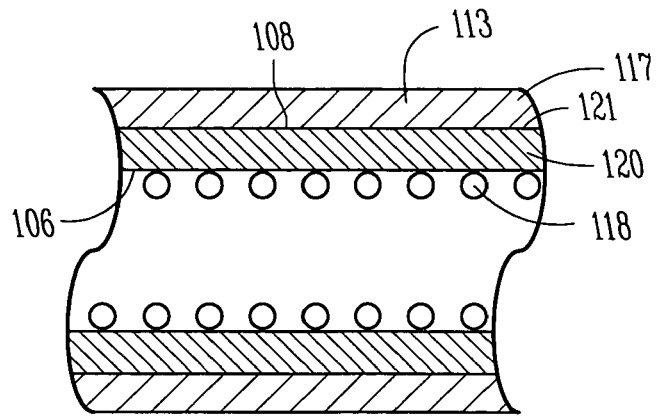
FIG. 2A illustrates a cross-sectional view of a portion of a lead assembly constructed in accordance with at least one embodiment.
Figure 2B:
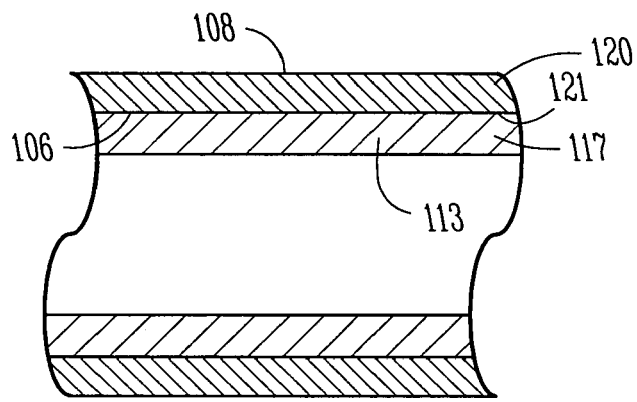
FIG. 2B illustrates a cross-sectional view of a portion of a lead assembly constructed in accordance with at least one embodiment.
Figure 2C:
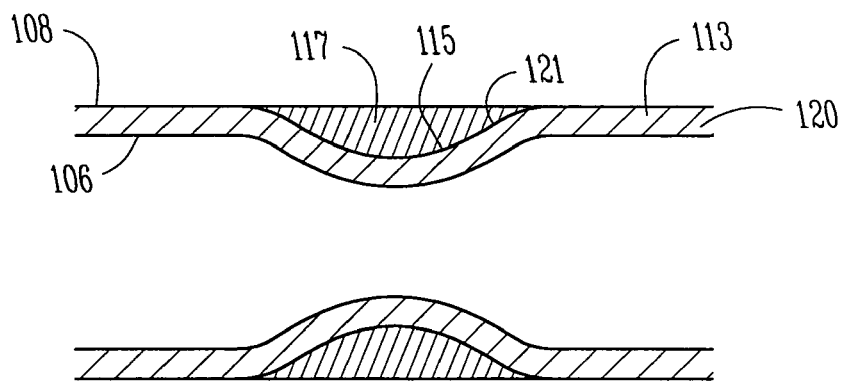
FIG. 2C illustrates a cross-sectional view of a portion of a lead assembly constructed in accordance with at least one embodiment.

FIGS. 2A, 2B, and 2C illustrate cross-sectional views of a portion of the lead body including a first layer of material 120. The lead body 113 further includes a second layer of material 117. The first layer of material 120, in one option, forms an insulative body to the lead. The first layer of material 120 is defined in part by an outer surface 108 and inner surface 106. In one option, the second layer of material 117 is disposed along only a portion, or continuously along an outer surface 108 of the first layer of material 120 to form the lead body 113, as illustrated in FIG. 2A. In another option, the second layer of material 117 is disposed along only a portion, or continuously along a length of the lead of the inner surface 106 of the first layer of material 120 to form the lead body 113, as illustrated in FIG. 2B. In yet another option, the first layer of material 120 of the lead body includes a variable outer diameter such as that shown in FIG. 2C.

In one option, the second layer of material 117 is disposed within a recess of the first layer of material 120. The recess 115 is formed, in one option, in an outer surface 108 of the first layer of material 120 of the lead body 113. The recess 115, in an option is treated with the adhesive enhancing surface 121, and allows for a coating of material, such as polymeric material therein. The recess 115 allows for the outer diameter, or portions of the outer diameter, to be coated with material, such as polyurethane or other materials, and yet further allows for the outer body to be formed isodiametrically. The recess 115 can be formed in a number of different manners. For example, the recess 115 can be formed using a die-stretching process.

The first layer of material 120 of the lead body, in one option, includes one or more activated surfaces 121. The activated surface 121 of the first layer of material 120 allows for the adhesiveness to be enhanced and allowing for coating of a second protective layer of material, for example, polymeric material to be coated thereon. The adhesive enhancing activated surface allows for two normally dissimilar substances to be coupled without the use of adhesive. The activated surface can be formed on the outer surface, and/or an inner surface, and/or portions along the outer and/or inner surfaces, and/or within recesses within either the outer surface and/or the inner surface of the first layer of material 120.

The activated surface of the first layer of material 120 can be activated in a number of different manners. In one option, the adhesive enhancing activated surface of the first layer of material 120 is produced by plasma surface modification or by plasma assisted or enhanced chemical vapor deposition treatment. The plasma treatment involves a number of steps. For example, the plasma treatment includes an optional first step of cleaning the surface to be activated, for example, at an atomic level. Suitable gases for the precleaning process include, but are not limited to, $O_2$, Ar, $N_2$, $CH_3OH$, and $CF_4$. The plasma treatment further includes a plasma deposition process with a gas, to form a tie layer. The plasma treatment further includes another step involved in the plasma enhanced deposition. This process involves functionalizing the surface, and thereby activating the surface, of the first layer of material 120 to increase the adhesiveness to that surface. Suitable monomers for treating the surface include but are not limited to, acrylic acid, allyl amine, acrylamide, acrylonitrile, methacrylic acid, glycidyl methacrylate, N,N-dimethylacrylamide, and acetylene.

The surface of the first layer of material 120 can be activated in other different manners, other than discussed above. For example, the adhesive enhancing activated surface of the first layer of material 120 can be produced by a chemical treatment to the first layer of material 120.

Once a surface of the first layer of material 120 has been activated, the first layer of material can be coated with a second layer of material, such as a polymeric material, for example, polyurethane. This provides a protecting coating to the first layer of material 120, where the first layer of material 120 forms an insulative coating. The second layer of material 117 can be applied in number of different manners. For example, the second layer of material can be coated onto the first layer of material. Coating can include dip coating or spray coating but is not necessarily so limited. Other examples of application include applying a second layer of material such as polyurethane by a melt process, or by applying with a tool such as a needle or brush, or spray coated.

Suitable materials for the first layer 120 and the second layer of material 117 are as follows. For example, the first layer of material can be formed of one or more of the following materials: silicone rubber, PTFE, ePTFE. The second layer of material 117 can be formed of polyurethane and/or other materials. In another option, the second layer is formed of a material that is more stiff than the first layer of material. The stiff changes can be disposed along all, a portion, or various portions of the lead. This allows for changes to the handling attributes of the lead as the stiffness of the lead can be modified along the lead. For example, an intermediate portion of the lead can be made more stiff than a distal end, decreasing risk of inadvertent penetration through a vessel wall or tissue. Furthermore, the handling attributes of the lead can be modified, including, but not limited to, thickness changes of the lead body.

FIG. 3 illustrates a flow diagram showing one example of how enhanced adhesion of a first layer of material, is achieved. As discussed above, one or more surfaces of the first layer of material 120 are activated to enhance its adhesiveness. Several embodiments include, but are not limited to, plasma surface modification, chemical treatment, and/or plasma assisted chemical vapor deposition treatment. It should be noted that one or more of the above processes may be used to form the activated surface. After the surface of the first layer of material is activated to enhance adhesion, the activated surface is coated with a second layer of material 117, such as a protective layer, for example, polyurethane. As discussed above, the coating can be done in a number of manners, including but not limited to spray coating, dip coating, or applied by a melt process.

Some example methods are as follows:

EXAMPLE #1

Silicone tubing is activated by a plasma process and subsequent plasma enhanced chemical vapor deposition of acrylic acid.

Next polyurethane solution is prepared using the following steps:
1. A flask is filled with dimethylacetamide (DMAC).
2. Polyurethane (Pellethane 2363-55D) is added to the DMAC solution.
3. The solution is stirred at a predetermined temperature, for a predetermined time, where a refluxing condenser maintains the volume of DMAC.
4. After the polyurethane has fully dissolved, the polyurethane-DMAC solution is removed from the flask.
5. DMAC is added to the stock solution to create a polyurethane-DMAC solution.

After preparing the solution the tubing can be dip coated. The previously prepared tubing is cut to length and is placed on a dip coater apparatus. This solution is transferred to a metal container and is used as the dipping container. The tubing is slowly cycled into and out of the polyurethane-DMAC solution. As or after the tubing comes out of the dipping solution, the tubing is subjected to heat.

EXAMPLE #2

The same process is used as in example #1 except an acetone/DMAC solution is used.

EXAMPLE #3

For spray coating, the same tubing preparation process can be used as described in example #1 and #2. Likewise, the solution is still prepared as described in example #1 and #2. In this case, however, a lower percentage of polyurethane is used in the final solution. In the spray coat process, the tubing is mounted on a mandrel. As the sprayer sprays the solution over the tubing, the tubing is rotated horizontally to maintain a uniform coating. Hot air is passed over the tubing to improve evaporation of the solvent during subsequent spray coats. Approximately 100 passes of 1% polyurethane solution create a 1 mil thick coating.

EXAMPLE #4

The dip coating process is performed as described in example #1. However, dimethylsulfoxide (DMSO) is used in place of DMAC.

EXAMPLE #5

To decrease the number of required dips or spray cycles (and thus manufacturing time) to achieve a given thickness coating, a higher percentage of polyurethane can be used in the above examples. To maintain the same viscosity the solution can be heated.

FIGS. 4 and 5 illustrate examples of use of the first and second layers of material within medical devices such as leads. FIG. 4 illustrates a side elevational view of the lead 110 that extends from a proximal end 112 to a distal end 114. In one option, the distal end 114 includes an active fixation device such as a helix. In another option, the lead 110 includes an electrode 116. The lead body 113, optionally, is formed so that it transitions from a single layer of material, such as silicone, to a combination of materials, such as silicone and polyurethane. The transition assists in allowing the distal end of the lead to be preformed in a variety of shapes, for example, without requiring the use of a wire. For example, the distal end 114 of the lead can be formed in a J-shape.

The lead body 113 can be formed in a subassembly such that the component can be partially formed and stocked to be used at a later date, or further processed at a later date. For example, a first layer of material 120 could be activated along the entire surface, or only along a partial amount of the surface, and stocked for further use at a later time. In another option, the entire first layer of material 120 can be activated, and only a portion of the first layer of material 120 can be coated with a second layer of material 117, and can be stocked in that form, to be used at a later date. In yet another option a distal portion 132 of the lead 110 includes only a first layer of insulative material, such as silicone, such that the distal end 114 can remain much more flexible than the remaining portions of the lead 110, which are coated with the protective layer of material 117. The distal portion 132 is disposed adjacent to the distal end 114 of the lead 110.

In an embodiment, the lead 110 further includes a transition portion that allows for the lead body to include portions with just the first layer of material 120 that transitions to a portion that includes a combination of the first layer of material 120 and the second layer of material 117. The transition portion is disposed along an intermediate portion 134 of the lead.

An intermediate portion 134 extends from the portion 132 to the proximal end of 112 of the lead. To form the transition portion, the first layer of material, such as silicone, is treated for example with the activation processes discussed above. The first layer of material is sprayed with a fine thin layer of polyurethane along the portion to form the transition portion. The polyurethane is fixed to the first layer of material via heat, laser, etc. to create the transition.

In yet another option, the second layer of material 117 is applied to the distal portion of the lead in order to facilitate creation of a structure, for example, such as a preformed J-shape or spiral shape. That is, the tubing formed by the first and second layers of materials themselves can be formed into a J-shape.

FIG. 5 illustrates a proximal portion of a lead 110, including a terminal end 140. The terminal end 140 includes a connector that is disposed within a header of a pulse generator (FIG. 1) disposed adjacent to the terminal portion is a portion 142 that includes the first and second layers of material, such as discussed above. For example, portion 142 includes a first layer having an activated surface, with a second layer of protective material, such as polyurethane. This allows for pocket abrasion resistance where most lead abrasion can occur. It should be noted that the sealing rings 144 are not affected due to selective application of the polyurethane coating to the portion 142 (e.g. via masking). The portion 142 is proximal to the terminal end portion near the proximal end of the lead 110. It should be noted that the coating of material is disposed on an activated surface, as discussed above. The coating of a second material such as polyurethane can be disposed on the terminal end in addition to disposing the material along other portions of the lead.

Advantageously, the activated surface allows for effective coating of materials such as polyurethane to dissimilar materials such as silicone, PTFE, or ePTFE. This allows for new configurations for leads, such as having a single component that transitions from a combination of materials, such as silicone and polyurethane, to a single material, such as silicone. This could reduce the overall number of parts, yet will provide abrasion resistance. Furthermore, the coating process will allow for the stiffness to be varied. The processes discussed and claimed herein allow for further manufacturing advantages. For example, the activation process can be done to a subassembly and stocked for use at a later date. Furthermore, the coatings of materials and combinations of material allow for a variety of shapes to be formed along the lead. For example, a J-shape at the distal end of the lead.

It is to be understood that the above description is intended to be illustrative, and not restrictive. For instance, the leads described above include, but are not limited to tachy, brady, or heart failure leads. It should be noted that features of the various above-described embodiments may be interchanged to form additional combinations. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An implantable cardiac lead comprising:
   an elongate sheath of a first layer of material, the first layer of material forming an insulative layer, the elongate sheath extending from a proximal end to a distal end, and having an intermediate portion therebetween, the elongate sheath defined in part by an outer surface and an inner surface;
   an elongate conductor located within the elongate sheath;
   the insulative first layer of material having at least one activated surface formed via a plasma assisted chemical vapor deposition treatment with one or more monomers or via chemical treatment;
   a second layer of material coated on the activated surface, the second layer of material including polyurethane; and
   wherein the at least one activated surface allows for the second layer of material to be coupled to the first layer of material without the use of adhesive.

2. The implantable cardiac lead of claim 1, wherein one or more portions of the distal end includes a coupling between the first layer of material and the second layer of material such that the distal end has a J-shape.

3. The implantable cardiac lead of claim 1, further comprising a terminal area including a connector, where the terminal area has an activated surface, and insulative coating is applied to the terminal area of the lead.

4. The implantable cardiac lead of claim 1, wherein the activated surface includes a recessed portion, and the second layer of material is disposed within the recessed portion.

5. The implantable cardiac lead of claim 4, wherein the lead is isodiametric.

6. The implantable cardiac lead of claim 1, wherein a body of the lead includes a transition portion transitioning from a combination of the first and second layers of material to the first layer of material only.

7. The implantable cardiac lead of claim 1, wherein the second layer of material is disposed along an intermediate portion and not at the distal end.

8. The implantable cardiac lead of claim 1, wherein the outer surface is a monomer treated outer surface.

9. The implantable cardiac lead of claim 8, wherein the monomer includes at least one of acrylic acid, allyl amine, acrylamide, acrylonitrile, methacrylic acid, glycidyl, N,N-dimethylacrylamide, and acetylene.

10. The implantable cardiac lead of claim 1, wherein the second layer comprises a lubricious coating disposed along the sheath.

11. The implantable cardiac lead of claim 1, wherein the first layer of material comprises one or a combination of silicone rubber, PTFE, or ePTFE.

12. The implantable cardiac lead of claim 1, wherein the second layer of material comprises silicone rubber in addition to polyurethane.

13. The implantable cardiac lead of claim 1, wherein the second layer of material is more stiff than the first layer of material.

14. An implantable cardiac lead comprising:
    an elongate sheath of an insulative polymeric material, the elongate sheath extending from a proximal end to a distal end, and having an intermediate portion therebetween, the elongate sheath defined in part by an outer surface and an inner surface;
    at least one elongate conductor located within the elongate sheath;
    the insulative polymeric material having an activated surface; and
    an abrasion resistant material coated on the activated surface of the elongate sheath and coupled thereto without the use of adhesive, the abrasion resistant material including polyurethane.

15. The implantable cardiac lead as recited in claim 14, wherein the activated surface is activated via a plasma assisted chemical vapor deposition treatment.

16. The implantable cardiac lead as recited in claim 14, wherein the outer surface is a monomer treated outer surface.

17. The implantable cardiac lead as recited in claim 16, wherein the monomer includes at least one of acrylic acid, allyl amine, acrylamide, acrylonitrile, methacrylic acid, glycidyl, N,N-dimethylacrylamide, and acetylene.

18. The implantable cardiac lead as recited in claim 14, wherein the elongate sheath includes a polyurethane coated surface.

19. The implantable cardiac lead as recited in claim 14, wherein the elongate sheath includes a silicone coated surface.

20. The implantable cardiac lead as recited in claim 14, further comprising a coating transition along the sheath.

21. The implantable cardiac lead as recited in claim 20, wherein the coating transitions from polyurethane and silicone to silicone only.

22. The implantable cardiac lead as recited in claim 14, wherein the sheath is pre-cleaned with one or more of $O_2$, Ar, $N_2$, methanol or $CF_4$.

23. The implantable cardiac lead as recited in claim 14, further comprising a terminal area including a connector, where the terminal area has an activated surface, and insulative coating is applied to the terminal area of the lead.

24. The implantable cardiac lead as recited in claim 14, wherein the activated surface includes a recessed portion.

25. The implantable cardiac lead as recited in claim 24, wherein the abrasion resistant material is disposed within the recessed portion.

26. The implantable cardiac lead as recited in claim 14, wherein the abrasion resistant coating comprises a lubricious coating disposed along the sheath.

27. The implantable cardiac lead of claim 14, wherein the distal end comprises one or more transitions between the insulative polymeric material and the abrasion resistant material such that the distal end includes a pre-formed J-shape or spiral shape.

28. An implantable cardiac lead comprising:
an elongate sheath of a first layer of material, the first layer of material forming an insulative layer, the elongate sheath extending from a proximal end to a distal end, and having an intermediate portion therebetween, the elongate sheath defined in part by an outer surface and an inner surface;
an elongate conductor located within the elongate sheath;
the insulative first layer of material having at least one activated surface;
a second layer coated on the activated surface; and
wherein the second layer of material is disposed along an intermediate portion of the elongate sheath and not at the distal end.

29. The implantabie cardiac lead as recited in claim 28, wherein the first layer of material comprises one or a combination of silicone rubber, PTFE, or ePTFE, and the second layer of material comprises one or a combination of polyurethane or silicone rubber.

30. An implantable cardiac lead comprising:
an elongate sheath of a first layer of material, the first layer of material forming an insulative layer, the elongate sheath extending from a proximal end to a distal end, and having an intermediate portion therebetween, the elongate sheath defined in part by an outer surface and an inner surface;
an elongate conductor located within the elongate sheath;
the insulative first layer of material having at least one activated surface;
a second layer coated on the activated surface, the second layer of material including polyurethane; and
wherein the outer surface is a monomer treated outer surface, the monomer including at least one of acrylic acid, allyl amine, acrylamide, acrylonitrile, methacrylic acid, glycidyl, N,N-dimethylacrylamide, and acetylene.

31. The implantable cardiac lead as recited in claim 30, wherein one or more portions of the elongate sheath includes a coupling between the first layer of material and the second layer of material such that the sheath includes a pre-formed J-shape or spiral shape.

32. An implantable cardiac lead comprising:
an elongate sheath of an insulative polymeric material, the elongate sheath extending from a proximal end to a distal end, and having an intermediate portion therebetween, the elongate sheath defined in part by an outer surface and an inner surface;
at least one elongate conductor located within the elongate sheath;
the insulative polymeric material having an activated surface;
an abrasion resistant material coated on the activated surface of the elongate sheath, the abrasion resistant material including polyurethane; and
wherein the outer surface is a monomer treated outer surface, the monomer including at least one of acrylic acid, allyl amine, acrylamide, acrylonitrile, methacrylic acid, glycidyl, N,N-dimethylacrylamide, and acetylene.

33. The implantable cardiac lead as recited in claim 32, wherein a body of the lead includes a transition portion transitioning from a combination of the insulative polymeric material and the abrasion resistant material to the insulative polymeric material only.

34. An implantable cardiac lead comprising:
an elongate sheath of an insulative polymeric material, the elongate sheath extending from a proximal end to a distal end, and having an intermediate portion therebetween, the elongate sheath defined in part by an outer surface and an inner surface;
at least one elongate conductor located within the elongate sheath;
the insulative polymeric material having an activated surface;
an abrasion resistant material coated on the activated surface of the elongate sheath; and
wherein the abrasion resistant material including polyurethane.

35. The implantable cardiac lead as recited in claim 34, wherein the abrasion resistant material is adapted to be coated on the activated surface via dip coating, spray coating, or a melt process.

36. The implantable cardiac lead of claim 34 wherein the elongate sheath is pre-cleaned with one or more of $O_2$, Ar, $N_2$, methanol or $CF_4$.

* * * * *

UNITED STATES PATENT AND TRADEMARK OFFICE
CERTIFICATE OF CORRECTION

PATENT NO. : 7,221,982 B2 Page 1 of 1
APPLICATION NO. : 10/889504
DATED : May 22, 2007
INVENTOR(S) : Aron et al.

It is certified that error appears in the above-identified patent and that said Letters Patent is hereby corrected as shown below:

In column 9, line 53, in Claim 29, delete "implantabie" and insert -- implantable --, therefor.

Signed and Sealed this

Seventh Day of August, 2007

JON W. DUDAS
*Director of the United States Patent and Trademark Office*